(12) United States Patent
Anderson et al.

(10) Patent No.: US 6,508,986 B1
(45) Date of Patent: Jan. 21, 2003

(54) DEVICES FOR USE IN MALDI MASS SPECTROMETRY

(75) Inventors: N. Leigh Anderson, Washington, DC (US); John Joseph Lennon, Gaithersburg, MD (US); Jack Goodman, Lusby, MD (US)

(73) Assignee: Large Scale Proteomics Corp., Germantown, MD (US)

( * ) Notice: Subject to any disclaimer, the term of this patent is extended or adjusted under 35 U.S.C. 154(b) by 118 days.

(21) Appl. No.: 09/644,780

(22) Filed: Aug. 24, 2000

Related U.S. Application Data
(60) Provisional application No. 60/151,075, filed on Aug. 27, 1999.

(51) Int. Cl.[7] .......................... B01L 11/00; B01L 59/44; G01N 1/10
(52) U.S. Cl. .......................... 422/100; 422/63; 422/65; 422/103; 250/288; 436/180; 73/864.25
(58) Field of Search ................. 422/100, 103, 422/930, 63, 65; 436/180; 73/864.25; 250/288

(56) References Cited

U.S. PATENT DOCUMENTS

| | | | | |
|---|---|---|---|---|
| 4,699,884 A | * | 10/1987 | Noss et al. ............. 422/100 X |
| 5,262,128 A | * | 11/1993 | Leighton et al. ............ 422/100 |
| 5,443,791 A | | 8/1995 | Cathcart et al. ............. 422/65 |
| 5,487,997 A | * | 1/1996 | Stolp ...................... 422/100 X |
| 5,719,060 A | | 2/1998 | Hutchens et al. ........... 436/174 |
| 5,882,930 A | | 3/1999 | Baier ........................ 436/49 |
| 5,888,831 A | | 3/1999 | Gautsch ..................... 436/177 |
| 5,993,627 A | | 11/1999 | Anderson et al. ........... 204/456 |
| 6,024,925 A | | 2/2000 | Little et al. ................ 422/100 |
| 6,124,137 A | | 9/2000 | Hutchens et al. ........... 436/155 |
| 6,132,582 A | | 10/2000 | King et al. ................. 204/604 |
| 6,175,112 B1 | | 1/2001 | Karger et al. .............. 250/288 |
| 6,267,930 B1 | * | 7/2001 | Ruediger et al. ....... 422/100 X |
| 6,287,872 B1 | | 9/2001 | Schurenberg et al. ....... 436/181 |
| 6,302,159 B1 | | 10/2001 | Ryan et al. ................. 141/4 |
| 6,362,004 B1 | | 3/2002 | Noblett ...................... 436/43 |

OTHER PUBLICATIONS

Lennon, John J., "Matrix Assisted Laser Desorption Ionization Time–of–Fight Mass Spectrometry", www.abrf.org, Jun. 1997, pp. 1–13.

* cited by examiner

*Primary Examiner*—Jill Warden
*Assistant Examiner*—John S. Starsiak, Jr.
(74) *Attorney, Agent, or Firm*—Roylance, Abrams, Berdo & Goodman, L.L.P.

(57) ABSTRACT

An alignment plate is provided with a plurality of holes for guiding a pipette tip toward a sample plate of a MALDI mass spectrometer. Each of the holes is provided with a conical upper contour in order to guide the pipette tip toward a specific location on the sample plate. Two companion alignment plates are used in order to overlay two separate arrays of samples on the sample plate. For instance, a first of two alignment plates is formed with a 10×10 array of holes so that a 10×10 array of samples is deposited by the pipette tip onto the sample plate. The second of the two alignment plates is formed with a 9×9 array of holes so that a 9×9 array of samples is deposited on the sample plate at locations offset from the 10×10 array of samples already on the sample plate. The number of samples loaded on the sample plate is large and the space on the sample plate is more fully utilized.

22 Claims, 15 Drawing Sheets

DEVICES FOR USE IN MALDI MASS SPECTROMETRY

This application claims priority to United States Provisional Application No. 60/151,075, filed Aug. 27, 1999.

BACKGROUND OF THE INVENTION

A. Field of the Invention

The invention relates to a method and apparatus for preparation of samples that are to be subjected to mass spectrometry analysis. Specifically, the invention relates to methods for preparing samples for mass spectrometry analysis and to plate-like members used to position samples on a sample plate for subsequent mass spectrometry analysis.

B. Background Information

Mass spectrometry devices measure the molecular mass of a molecule by measuring the molecule's flight path through a set of magnetic and electric fields. Such devices are well known and are widely used in the field of biomolecular research. In proteomics research, for instance, mass spectrometry is used to identify proteins.

Proteins are typically separated from one another by electrophoresis, such as the techniques described and claimed U.S. Pat. No. 5,993,627 to Anderson et. al. (the Anderson et. al. patent), which is incorporated herein by reference in its entirety. For instance, as set forth in the Anderson patent, a tissue sample is first subjected to a first dimension electrophoresis process where groups of proteins are separated linearly within a tubular gel filled column. The first dimension separation of proteins is then inserted along an edge of a flat planar gel slab and subjected to a second dimension of electrophoresis thereby generating a two dimensional pattern of spots formed by clusters of proteins that have moved to respective iso-electric focusing points. Thereafter, selected proteins are excised from the second dimension gel slab for further study. The selected excised spots are next prepared for analysis using, for instance, mass spectrometry.

An increasingly used technique for studying biological molecules includes the use of MALDI mass spectrometry apparatus (matrix-assisted laser desorption ionization apparatus) where the biological sample is embedded in a volatile matrix and is vaporized by being subjected to an intense laser emission. One such MALDI apparatus is a MALDI-TOF apparatus (TOF is time-of-flight spectrometry). In the field of proteomics, mass spectrometry, and in particular, MALDI-TOF techniques are used to determine the molecular weight of peptides produced by digestion of isolated proteins. One such MALDI-TOF apparatus is VOYAGER DE STR Biospectrometry Workstation manufactured and sold by APPLIED BIOSYSTEMS.

FIG. 1 depicts a generic MALDI-TOF apparatus that includes a frame 1 that supports the electronic and computer equipment necessary to control a laser 5. The laser 5 is aimed at a fixed location in a positioning mechanism 10. The positioning mechanism 10 includes means (not shown) for positioning a sample in the line of fire of the laser 5. Typically in a MALDI-TOF apparatus, the laser is fixed in place and the sample is moved into position for analysis. The depicted MALDI-TOF apparatus includes a small removable sample plate 15, shown in FIG. 2, that fits into the positioning mechanism 10. Typically, the sample plate 15 is insertable into a slot 20 in the positioning mechanism 10 of the MALDI-TOF apparatus and is thereafter held in a specific orientation within the positioning mechanism 10 for sample analysis. The sample plate 15 typically holds a plurality of discrete samples on one surface thereof, with the samples being spaced apart from one another. The sample plate 15 includes guide members 15a, guide holes 15b and alignment pin 15d that are used by corresponding members (not shown) within the positioning mechanism 10 for positioning and moving the sample plate 15 with respect to the line of fire of the laser 5.

The samples are typically loaded onto the sample plate 15 by a separate device or robotic apparatus, such as the X-Y robotic apparatus depicted in FIG. 3. Such X-Y robotic apparatuses are typically manufactured and sold with each specific mass spectrometry apparatus. The X-Y robotic apparatus depicted in FIG. 3 includes a recess that retains the sample plate 15 in position for sample loading. The X-Y robotic apparatus includes a first arm 30 that moves back and forth along an X axis and a second arm 40 that moves along a Y axis defined along the length of the first arm. The second arm 40 supports a pipette tip 45 that is used to spot samples on the sample plate 15. Specifically, the pipette tip 45 is moved by the first and second arms 30 and 40 to a position above a 96-well plate 50 (or other similar sample holder) or microcentrifuge tubes and the pipette tip 45 picks up a sample from the 96-well plate 50 or microcentrifuge tubes. The pipette tip 45 is then moved to a location above the sample plate 15 and the sample is spotted on the specified location of the sample plate.

Typically, an array of samples are spotted on the sample plate 15 at predetermined locations. After the array of samples are loaded onto the sample plate 15, the sample plate 15 is inserted into the slot 20 of the MALDI apparatus. Using an imaging system 25 focused on the sample plate 15 within the MALDI apparatus, in combination with the positioning mechanism 10, the laser beam from the laser 5 can be aimed, one by one, at the sample(s) on the sample plate 15.

The mass spectrometry apparatus typically takes several hours to analyze an array of samples on the sample plate 15. Therefore, in order to minimize human involvement, automation of the process is critical. The locations of the samples are typically pre-programmed into the computer that controls the MALDI-TOF apparatus so that during the analysis of the samples, the positioning mechanism 10 automatically repositions the sample plate 15 into the line of fire of the laser 5. Therefore, if any of the samples on the sample plate 15 are not properly positioned, the laser 5 is not likely to hit each of the samples. For instance, on the sample plate 15 depicted in FIG. 2, a 10×10 array of samples is positioned on the upper surface at spaced apart intervals. The positioning mechanism 10 moved into a target position with respect to centers of the desired location of each spot. The desired location of each spot assumes that center of each of the spots in the 10×10 array is constant.

Unfortunately, there are several shortcomings associated with the above described X-Y robotic apparatus (FIG. 3). Although the positioning mechanism 10 within the MALDI apparatus has positional accuracy with respect to movement of the sample plate 15, the X-Y robotic apparatus typically sold with a MALDI apparatus is not as precise with respect to accurate spotting or depositing of samples on the sample plate 15. Specifically, the spots in a 10×10 array of samples do not wind up being centered on the desired center targeted by the positioning mechanism 10. The array of 10×10 samples may have some samples that are accurately centered, and other samples that are off center by as much as half the width of the sample.

Part of the problem with such X-Y robotic apparatuses relates to the replaceable pipette tips 45 used to retrieve a sample and deposit the sample onto the sample plate 15. The pipette tips are not perfectly uniform in size and shape. Further, the tips are deformable and hence accurate positioning of samples is not possible. As well, the X-Y robotic apparatus may not have movement and location capabilities as precise as the movement and location capabilities of the positioning mechanism 10 of the MALDI apparatus.

Another problem relates to the pre-programmed settings for locating samples on sample plates 15 of such X-Y robotic apparatuses. Specifically, X-Y robotic apparatuses are not programmed to maximize the use of the space of the surface of the sample plate 15. For instance, each pair of adjacent samples in the 10×10 array of samples mentioned above is typically spaced apart by a distance greater than the diameter of the sample. There is a substantial amount of empty space on the surface of the sample plate 15 even with a 10×10 array of samples. Since the MALDI-TOF apparatus takes considerable time to analyze samples and requires human interaction to switch sample plates 15 in the mass spectrometer, it is advantageous to analyze as many samples as possible on a single sample plate. Current technology limits the number of samples that can be analyzed on a single sample plate 15.

There is a need for more precise positioning of samples on a sample plate and a need for maximizing the space on a sample plate in order to more efficiently utilize a mass spectrometry apparatus.

SUMMARY OF THE INVENTION

One object of the present invention is to provide a means for more precisely depositing samples on a sample plate of a mass spectrometry apparatus.

Another object of the present invention is to provide a means for maximizing the number of samples spotted on the surface of a sample plate of a mass spectrometry apparatus.

An aspect of the present invention relates to the use of an alignment plate to assist in accurate positioning of a pipette tip delivering samples onto a sample plate of a mass spectrometer.

Another aspect of the present invention relates to the use of an adaptor plate and an alignment plate with an X-Y manipulator device originally designed for liquid sample manipulation. Use of the adaptor plate and alignment plate of the present invention allows for new usage of the X-Y manipulator device. Specifically, the X-Y manipulator device can be used for spotting samples on a sample plate of a mass spectrometer with the alignment providing alignment holes for accurate positioning of samples on the sample plate.

In accordance with yet another aspect of the present invention, a plurality of alignment plates are used to guide a pipette tip toward a sample plate for accurate positioning of samples on the sample plate. A first alignment plate guides the pipette tip to spot an array of samples on the sample plate. After replacing the first alignment plate with a second alignment plate, a second array of samples can be used to guide the pipette tip to spot a second array of samples on the sample plate, where the second array of samples are located between, but offset from the first array of samples thereby maximizing the number of samples positionable on the sample plate.

DETAILED DESCRIPTION OF THE INVENTION

Figure 4:
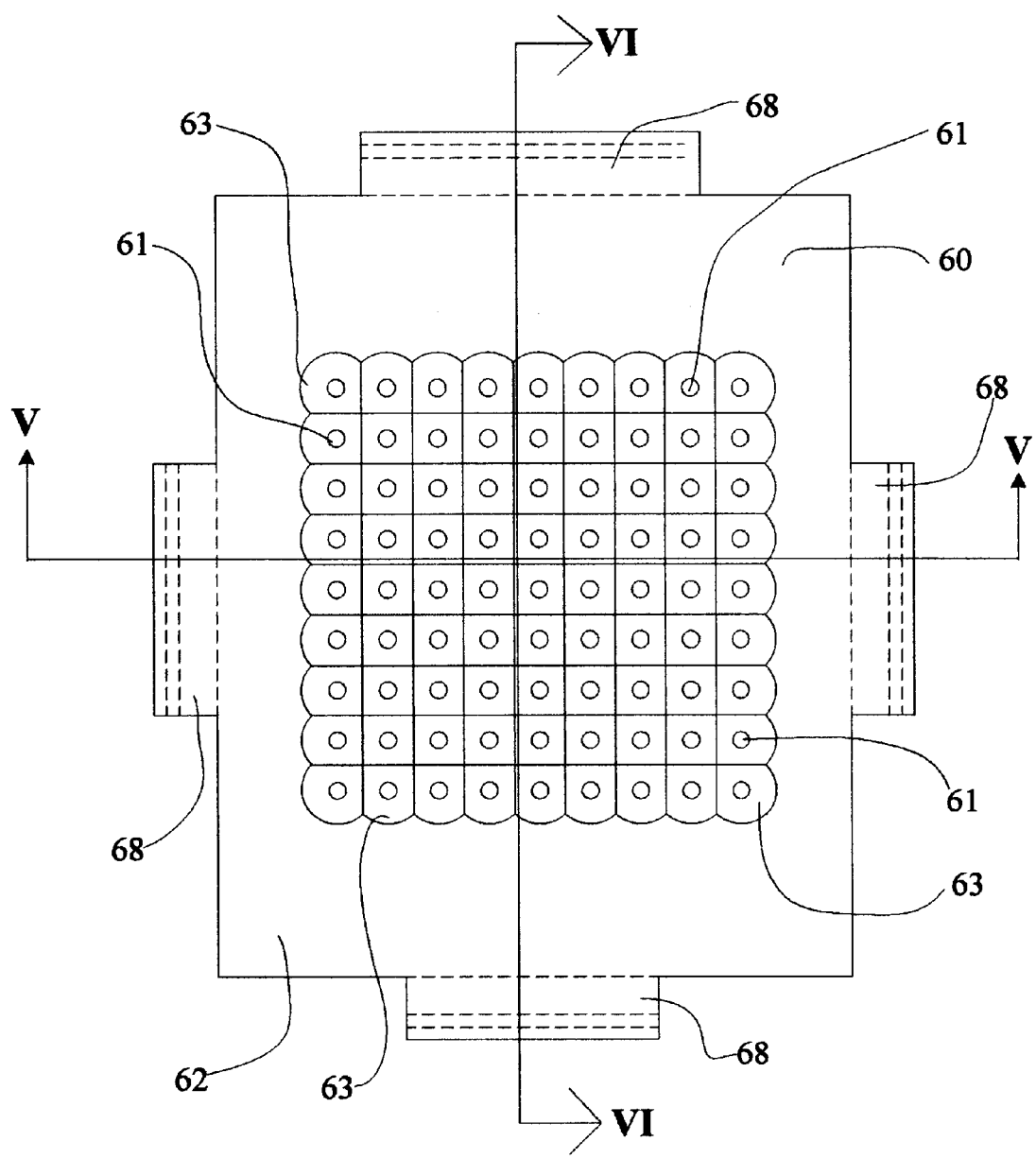
FIG. 4 is top view of an alignment plate having a 10×10 array of alignment holes used for positioning samples on a sample plate in accordance with one embodiment of the present invention.

The present invention relates to alignment plates that include holes for guiding a pipette tip toward a sample plate thereby assisting in accurately spotting or depositing samples on a sample plate of a mass spectrometry apparatus. FIG. 4 is top view of an alignment plate 60 that is formed with a plurality of holes 61 that define an array of holes. In the embodiment depicted in FIG. 4, there are one hundred holes 61 defining a 10×10 array of alignment holes used for positioning samples on a sample plate 15 in accordance with one embodiment of the present invention.

Each of the holes 61 extends from an upper surface 62 of the alignment plate 61 to a lower surface 65. At the upper surface 61, each hole 61 is further provided with a conical contour 63 whose function is described in greater detail below. The alignment plate 61 is further formed with a plurality of positioning legs 68 that extend downward away from the upper surface 62.

Figure 1:
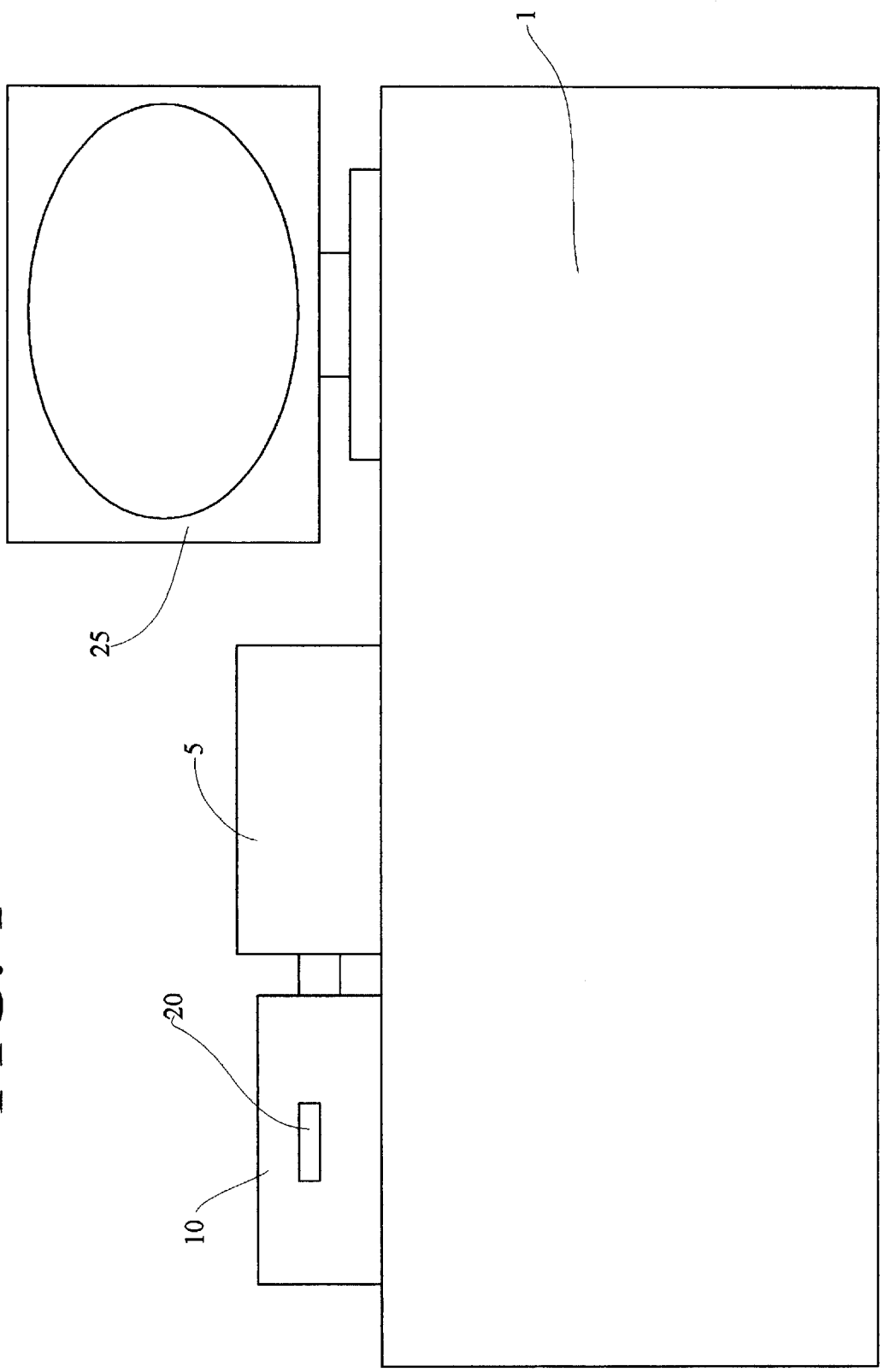
FIG. 1 is a side schematic view of a mass spectrometry apparatus.
Figure 2:
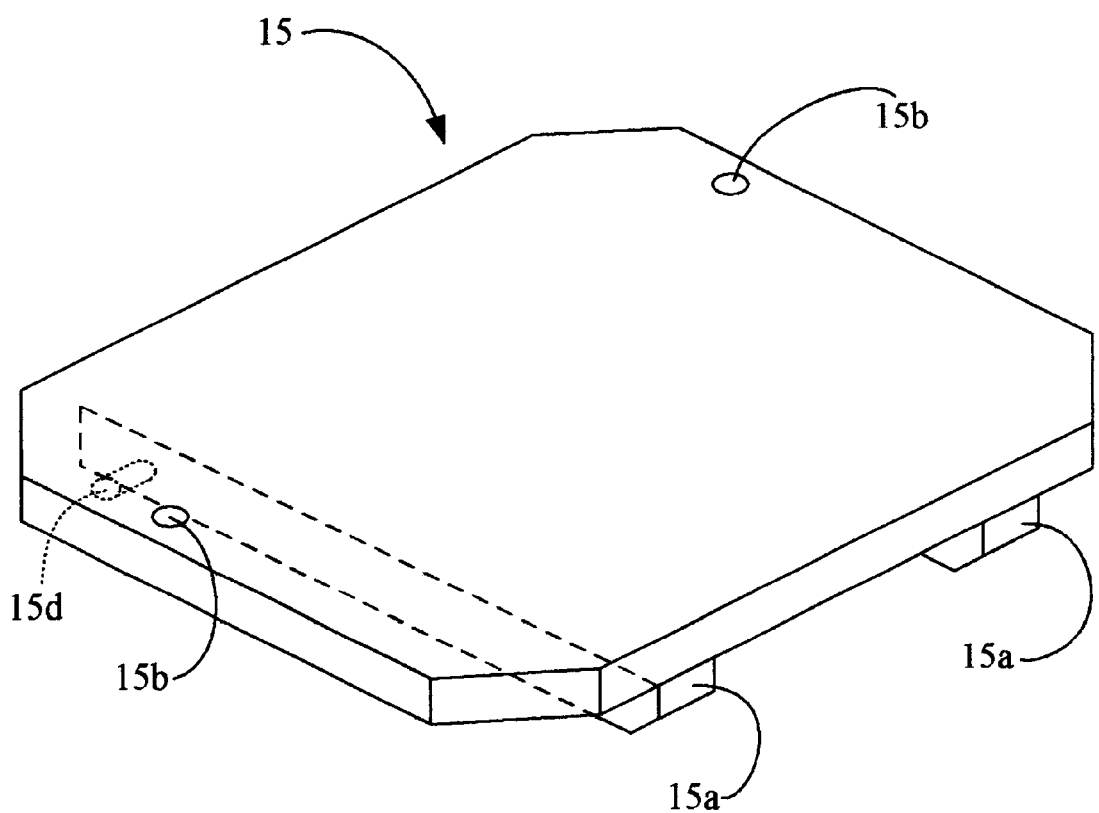
FIG. 2 is a perspective view of a sample plate for samples to be analyzed in the mass spectrometry apparatus depicted in FIG. 1.
Figure 3:
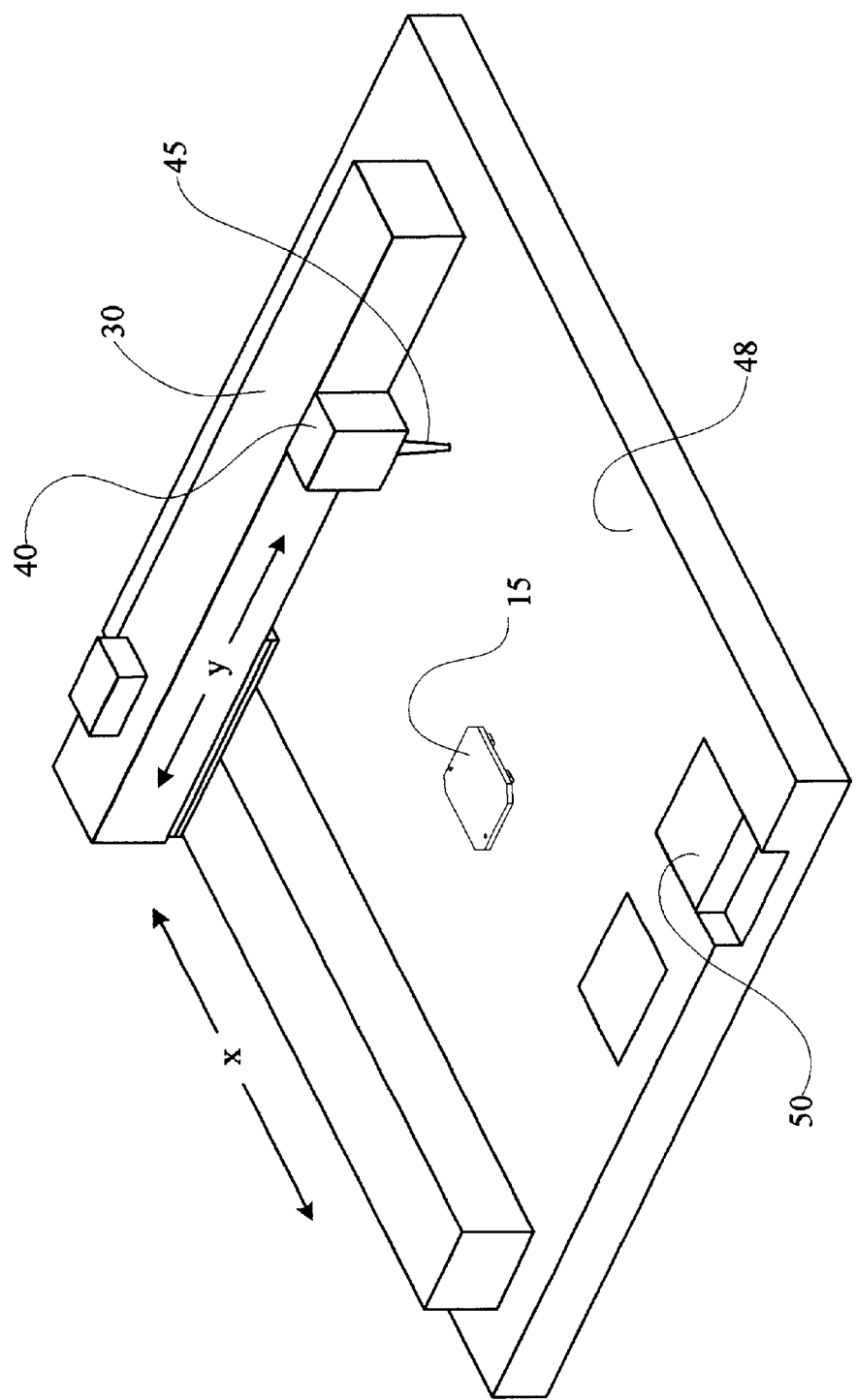
FIG. 3 is a perspective view of an X-Y robotic apparatus used to spot samples on the surface of the sample plate depicted in FIG. 2.
Figure 5:
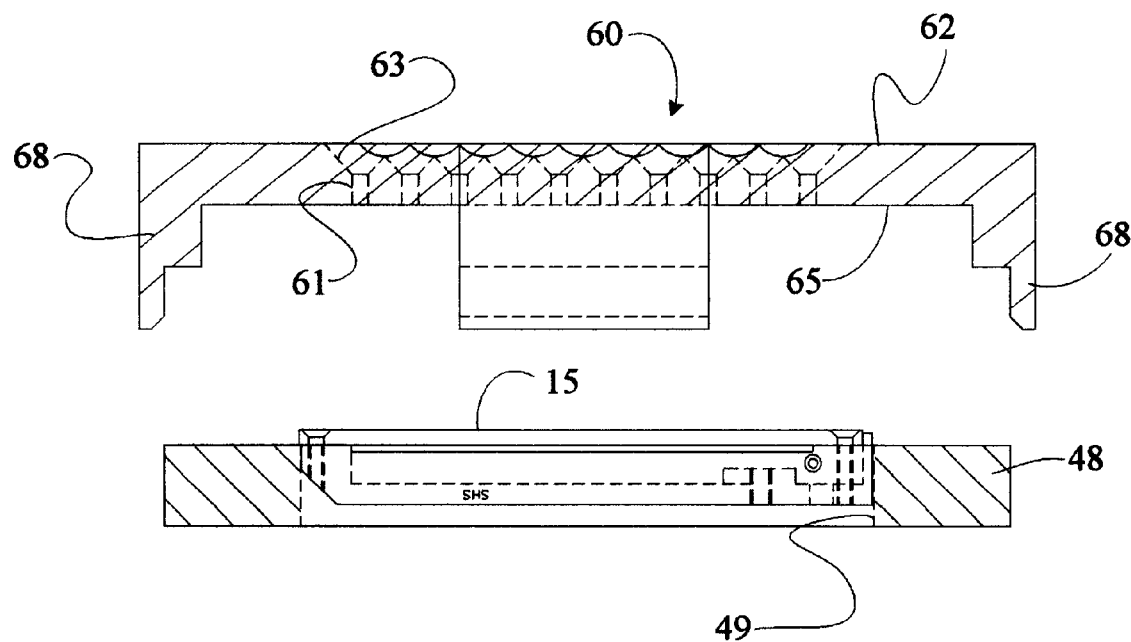
FIG. 5 is side exploded cross-section view taken along the line V—V in FIG. 4 showing the sample plate mounted on the table of an X-Y robotic apparatus, with the alignment plate depicted in FIG. 4 being mounted thereon in accordance with the present invention.
Figure 6:
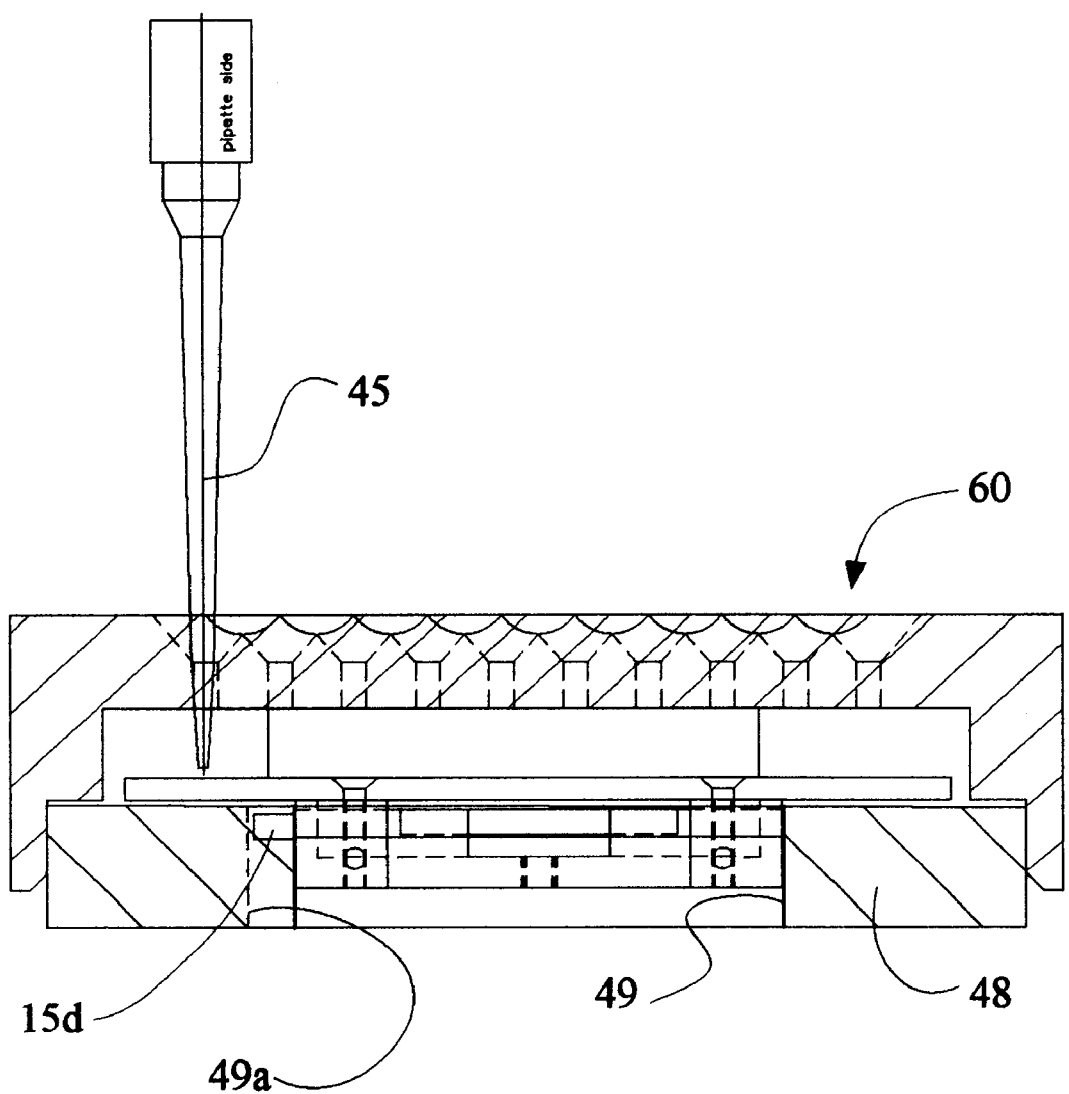
FIG. 6 is a side cross-section view taken along the line VI—VI in FIG. 4 showing the sample plate mounted on the table of an X-Y robotic apparatus, with the alignment plate depicted in FIGS. 4 and 5 mounted thereon, and a pipette delivering a sample through a hole in the alignment plate to the surface of the sample plate in accordance with the present invention.

The X-Y robotic apparatus described above with respect to FIG. 3 is typically formed with means for retaining the sample plate 15. Specifically, the X-Y robotic apparatus includes a table 48 that includes a recess 49 for receiving the sample plate 15, as shown in FIGS. 5 and 6. The recess 49 snuggly receives the sample plate 15 thereby retaining the sample plate 15 in a stationary position. The alignment plate 60 and its positioning legs 68 are formed to conform to the surface contours of the table 48 such that the sample plate 15 may be sandwiched in between the table 48 and the alignment plate 60, as depicted in FIG. 6. The positioning legs 68 firmly engage the contours of the table 48 such that the alignment plate 60 is held in a stationary position above the sample plate 15, as depicted in FIG. 6. Alternatively, the positioning legs 68 may be dimensioned to contact the outer edges of the sample plate 15.

Figure 7:
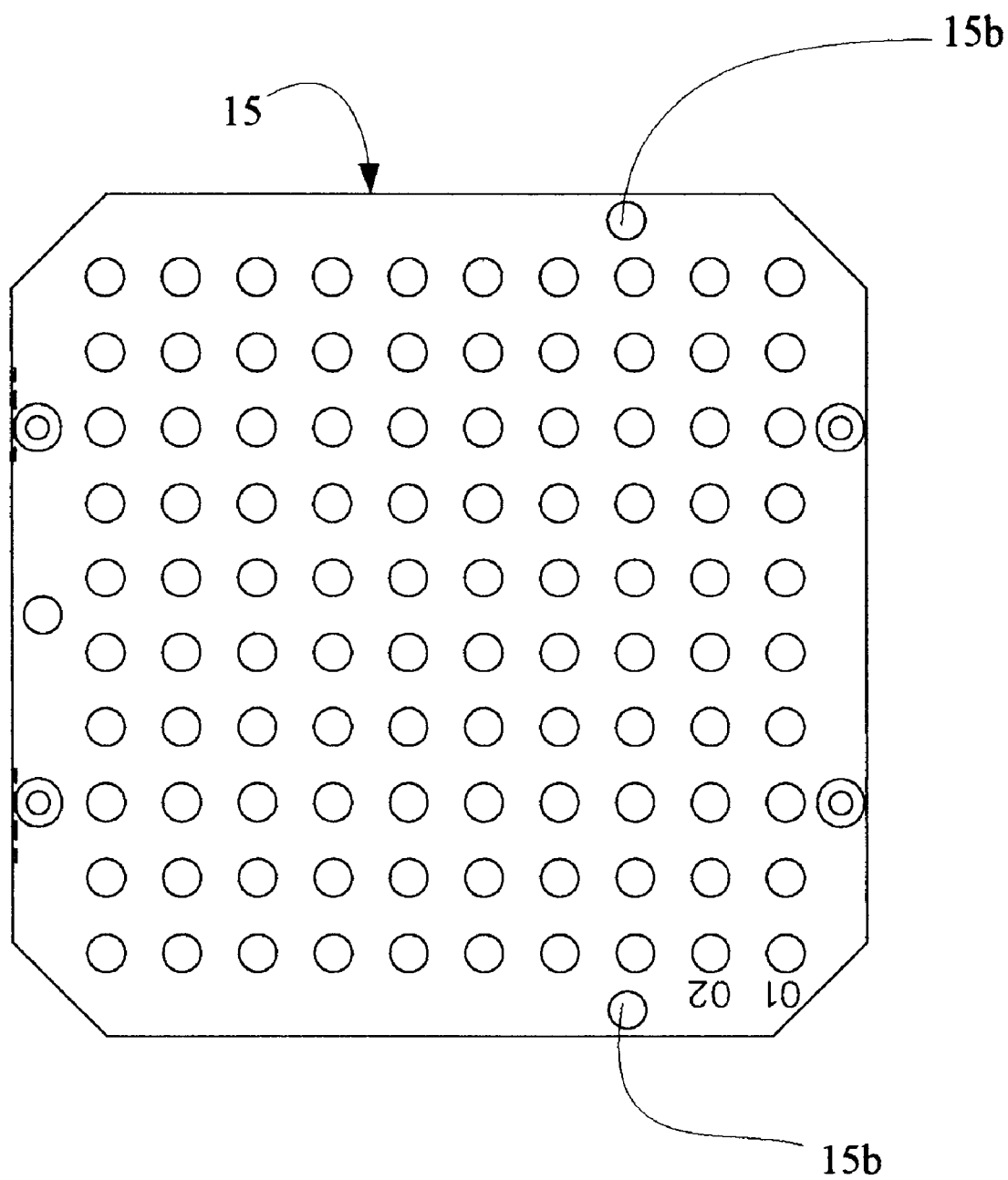
FIG. 7 is a top view of the sample plate with an array of 10×10 samples accurately positioned on the upper surface thereof in accordance with the present invention.

FIG. 6 is a side view showing the sample plate mounted on the table of the X-Y robotic apparatus, with the alignment plate 60 mounted thereon. A pipette tip 45 is shown extending through one of the holes 61 in the alignment plate 60 delivering the sample to the upper surface 62 of the sample plate 60. As described above, the X-Y robotic apparatus depicted in FIG. 3 positions the pipette tip 45 above the sample plate 15 in order to deposit a sample. With the alignment plate 60 positioned above the sample plate 15, as the X-Y robotic apparatus moves the pipette tip 45 downward toward the sample plate 15, the pipette tip 45 engages the conical contour 63 of the hole 61 in the alignment plate 60. As the pipette tip 45 contacts the conical contour 63, it is guided into the hole 61 and toward the upper surface of the sample plate 15. Since the alignment plate 60 is finely machined with the centers of the holes 61 in the 10×10 array at accurate, predetermined distances from one another, the samples are reliably positioned with respect to one another, as shown in FIG. 7. FIG. 7 is a top view of the sample plate 15 with an array of 10×10 samples accurately positioned on the upper surface of the sample plate 15. In other words, the pipette tip 45 is guided into and through the holes 61 in the alignment plate 60 in order to more reliably position the samples on the sample plate 15.

It should be understood that the alignment plate 60 depicted in FIGS. 4 and 5 is not limited to the 10×10 array of holes 61. Alternatively, a greater number of holes may be formed. For instance, the inventors have made an alternate embodiment of the alignment plate that has a 17×17 array of holes (not shown).

It should further be appreciated that the X-Y robotic apparatus and the replaceable pipette tips are guided into position by the conical contour 63 of the holes 61 in order to deposit samples on the sample plate 15. Therefore, positional accuracy of the X-Y robotic apparatus and deformable nature of the pipette tips 45 are no longer so critical because positional accuracy is now provided by the alignment plate 60.

Figure 8:
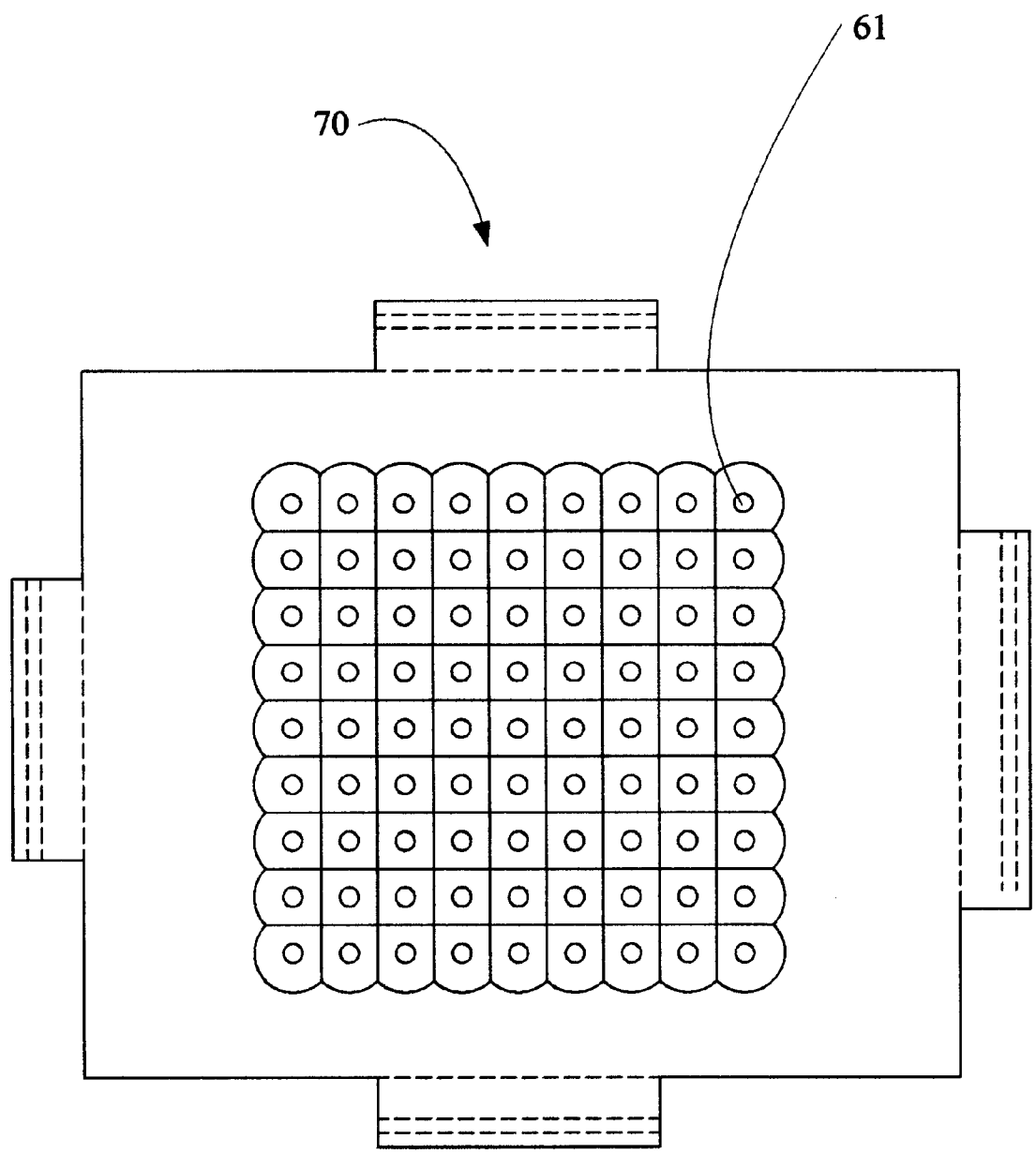
FIG. 8 is top view of a second alignment plate having a 9×9 array of alignment holes used for positioning samples on a sample plate in accordance with the present invention, with the 9×9 array of alignment holes being located to compliment the 10×10 array of holes in the alignment plate depicted in FIG. 4.
Figure 9:
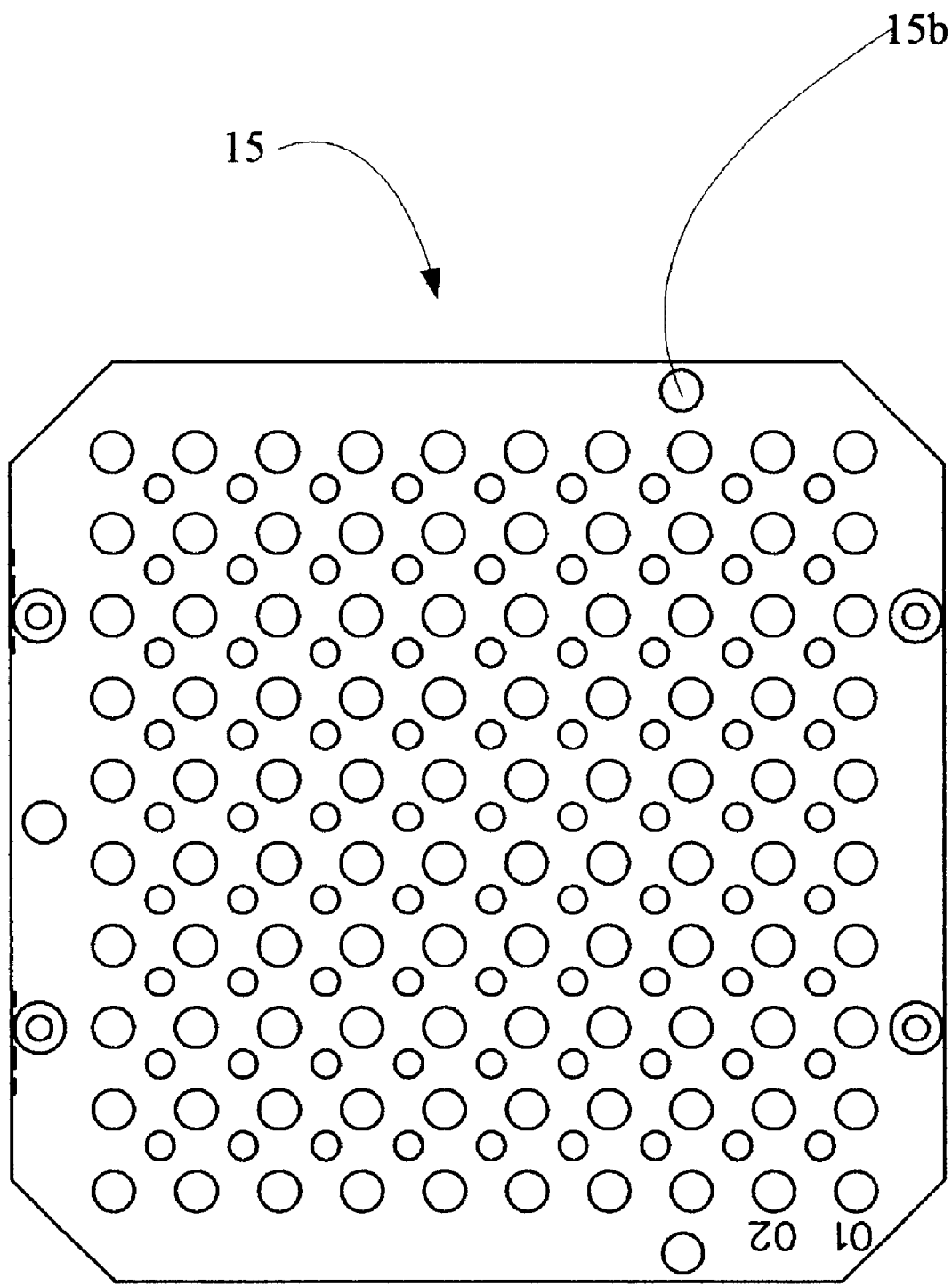
FIG. 9 is another top view of the sample plate depicted in FIG. 7 with the array of 10×10 samples accurately positioned on the upper surface thereof along with an additional 9×9 array of samples loaded using the alignment plate depicted in FIG. 8 in accordance with the present invention.

FIG. 8 is top view of a second alignment plate 70 having a 9×9 array of alignment holes used for positioning samples on the sample plate 15 in accordance with an additional feature of the present invention. The 9×9 array of alignment holes 61 are located to compliment the 10×10 array of holes in the alignment plate 60 depicted in FIG. 4. Specifically, after the 10×10 array of samples is deposited on the sample plate 15, as shown in FIG. 7, the alignment plate 60 is removed from the table 48. The second alignment plate 70 is then installed on the table 48 above the sample plate 15 having the 10×10 array of samples (FIG. 7) deposited thereon. An additional eighty-one (81) samples are then deposited on to the sample plate 15 to form the two space apart arrays of samples on the sample plate 15, as shown in FIG. 9. In other words, first the alignment plate 60 is used to accurately position the pipette tip 45 above the sample plate 15 in order to deposit a 10×10 array of samples on the sample plate 15. Thereafter, the second alignment plate 60 is used to accurately position the pipette tip 45 above the sample plate 15 in order to deposit an additional 9×9 array of samples between the 10×10 array of samples, as depicted in FIG. 9.

It should be understood that the second alignment plate 70 can have any number of holes in order to complement the holes in the first alignment plate 60. For instance, if the first alignment plate 60 is provided with a 12×12 array of alignment holes, the second alignment plate 70 is provided with either a 11×11 array of alignment holes or a 13×13 array of alignment holes to significantly increase the number of samples deposited on the sample plate 15. Further, the second alignment plate 70 described above and shown in the drawings includes an array of holes that are configured to be diagonally offset from the holes in the first alignment plate. Alternatively, the array of holes in the second alignment plate may be offset from the holes in the first plate along one axis, not diagonally offset. Further, a series of alignment plates can be configured to assist in spotting three or four separate arrays of spots on a sample plate, with the alignment holes in each alignment plate being offset from the other alignment plate holes.

Figure 10:
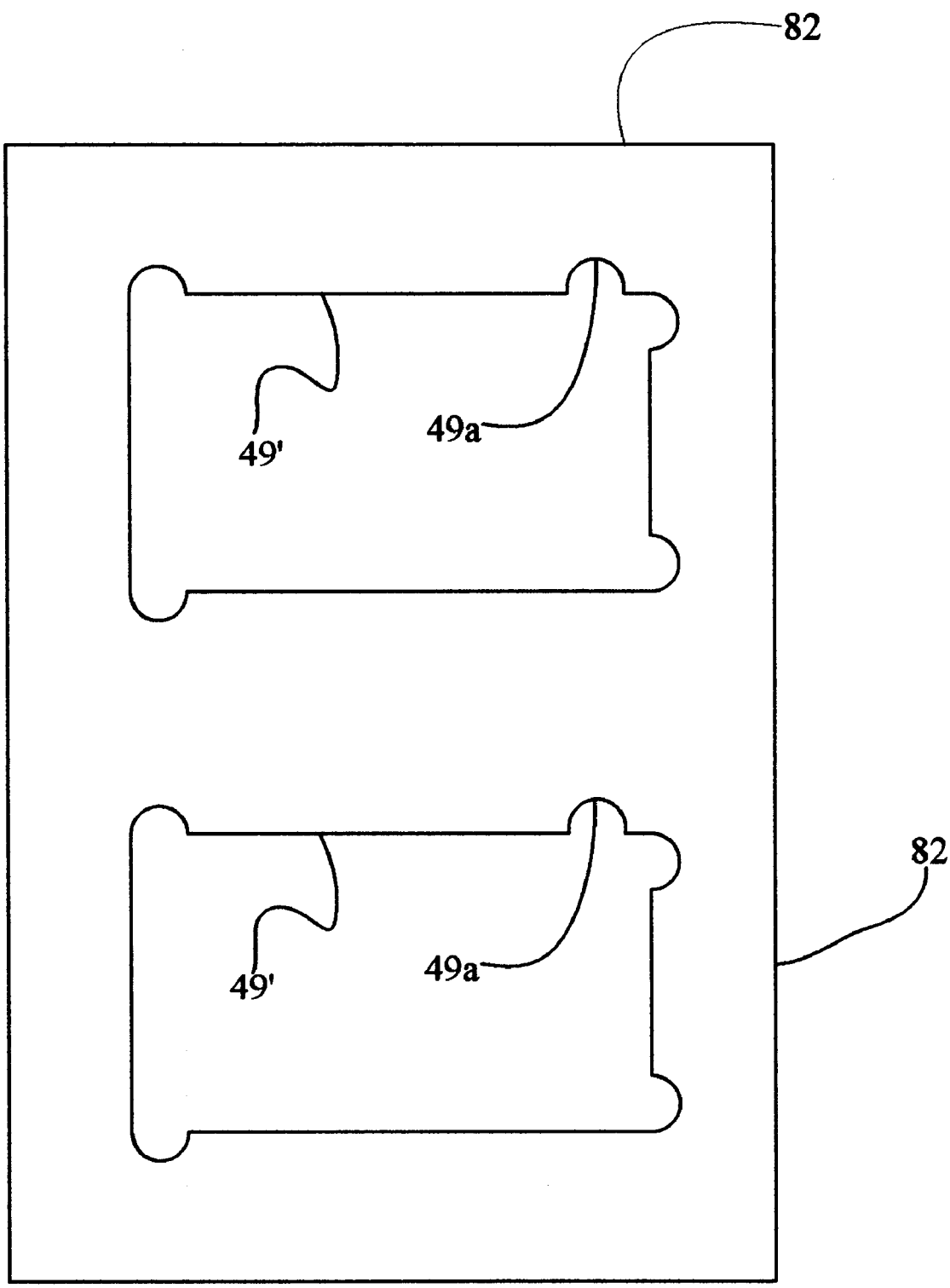
FIG. 10 is a top view of an adaptor plate for use with various types of X-Y robotic apparatus in accordance with a second embodiment of the present invention.

In a second embodiment of the present invention, the sample plate 15 is loaded with samples by an X-Y robotic apparatus that is not provided with a recess for retaining the sample holder 15. Instead, an adaptor plate 80 depicted in FIG. 10 is used to retain the sample holder 15. Specifically, the adaptor plate 80 has an outer perimeter 82 that is formed with dimensions corresponding to retainer portions 85 (shown in FIGS. 13 and 14) on an X-Y robotic apparatus. The adaptor plate 80 is provided in order to deposit samples on the sample plate 15 using an X-Y robotic apparatus that is not originally manufactured for use with a MALDI-TOF apparatus.

FIG. 10 is a top view of the adaptor plate 80. The adaptor plate 80 is formed with at least one recess 49' that is shaped to securely receive and retain the sample plate 15. The recess 49' and the recess 49 described above have generally the same shape. The recess 49' (and the recess 49 in FIGS. 5 and 6) includes an alignment recess 49d that receives an alignment pin 15d such that the sample plate 15 only fits into the recess 49' in a single orientation.

The adaptor plate 80 is formed with two recesses 49' but could be formed with more than two recesses 49' providing the adaptor plate 80 is large enough to receive such recesses.

The size of the adaptor plate 80 is dependent upon the size of the retainer portions 85 of the X-Y robotic apparatus, since the adaptor plate 80 is made to be received in the retainer portions 85.

Figure 11:
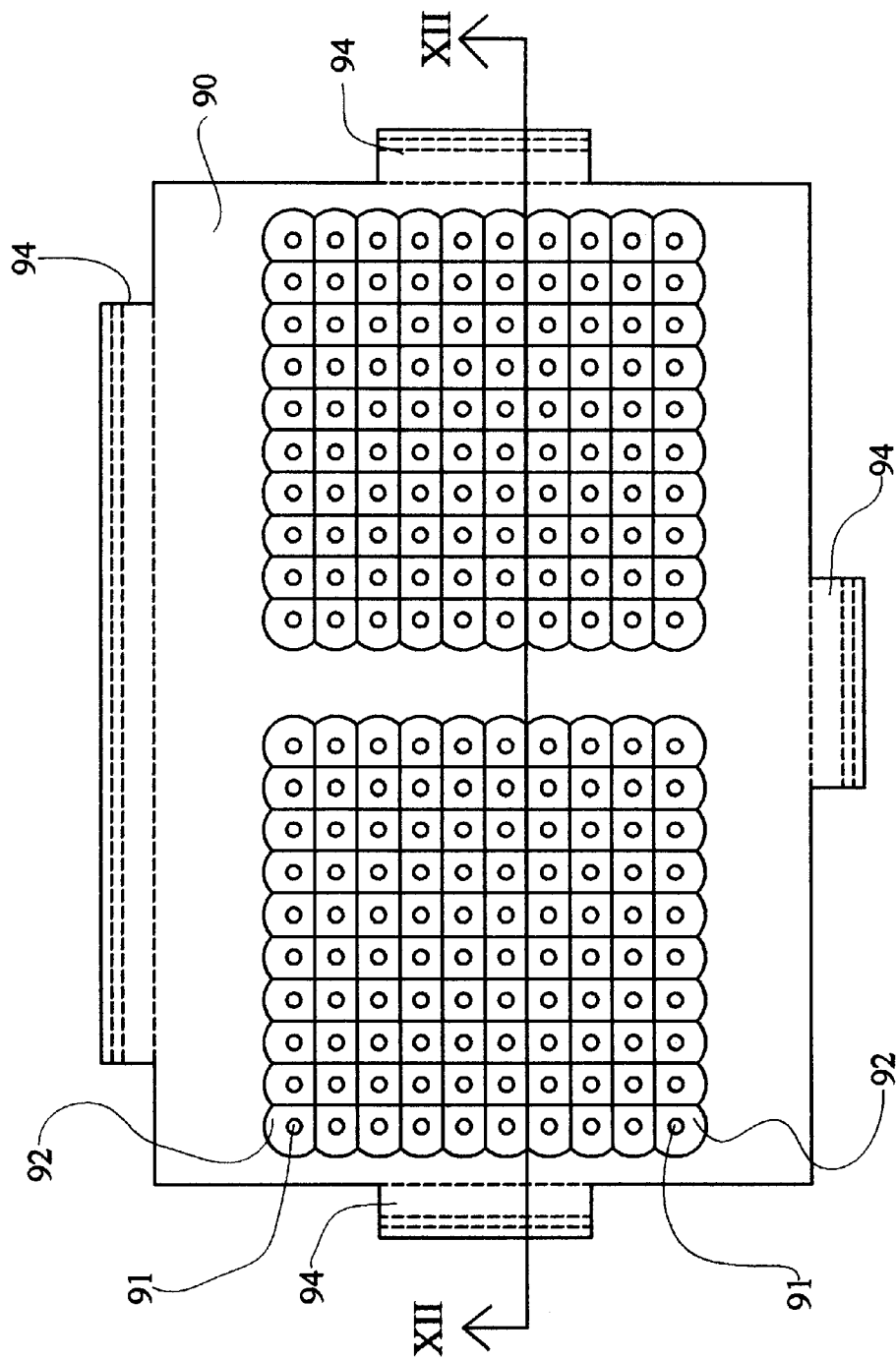
FIG. 11 is a top view of an alignment plate in accordance with the second embodiment of the present invention.

A first alignment plate 90 shown in FIG. 11, is dimensioned to correspond to the size and shape of the adaptor plate 80. Since the adaptor plate 80 is formed with two recesses 49' to receive and securely retain two sample plates 15, the first alignment plate 90 is formed with two separate 10×10 arrays of alignment holes 91. Each two 10×10 arrays of alignment holes 91 corresponds to one of the sample plates 15. Each alignment hole 91 is formed with a conical contour 92 to guide a pipette as the pipette deposits a sample on the sample plate 15. The first alignment plate 90 is further formed with positioning legs 94 for holding the first alignment plate 90 on the adaptor plate 80.

Figure 12:
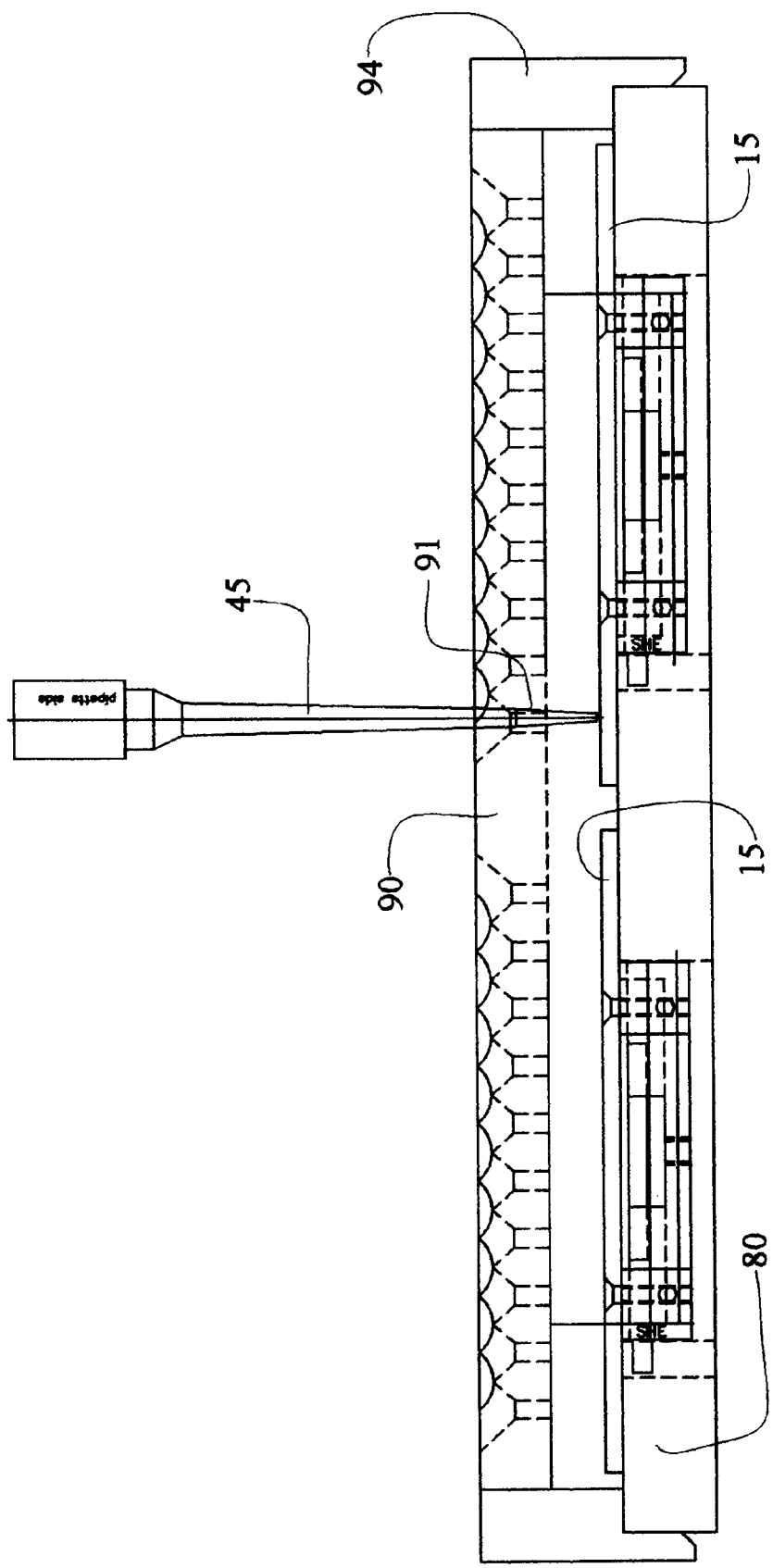
FIG. 12 is a side view showing two sample plates mounted on the adaptor plate depicted in FIG. 10, with the alignment plate depicted in FIG. 11 mounted thereon, and a pipette delivering a sample through a hole in the alignment plate to the surface of one of the sample plates in accordance with the present invention.

FIG. 12 is a slightly exploded side view showing two sample plates 15 mounted on the adaptor plate 80, with the first alignment plate 90 depicted in FIG. 11 mounted thereon. A pipette tip 45 is shown extending through one of the alignment holes 91 depositing a sample on surface of one of the sample plates 15.

Figure 13:
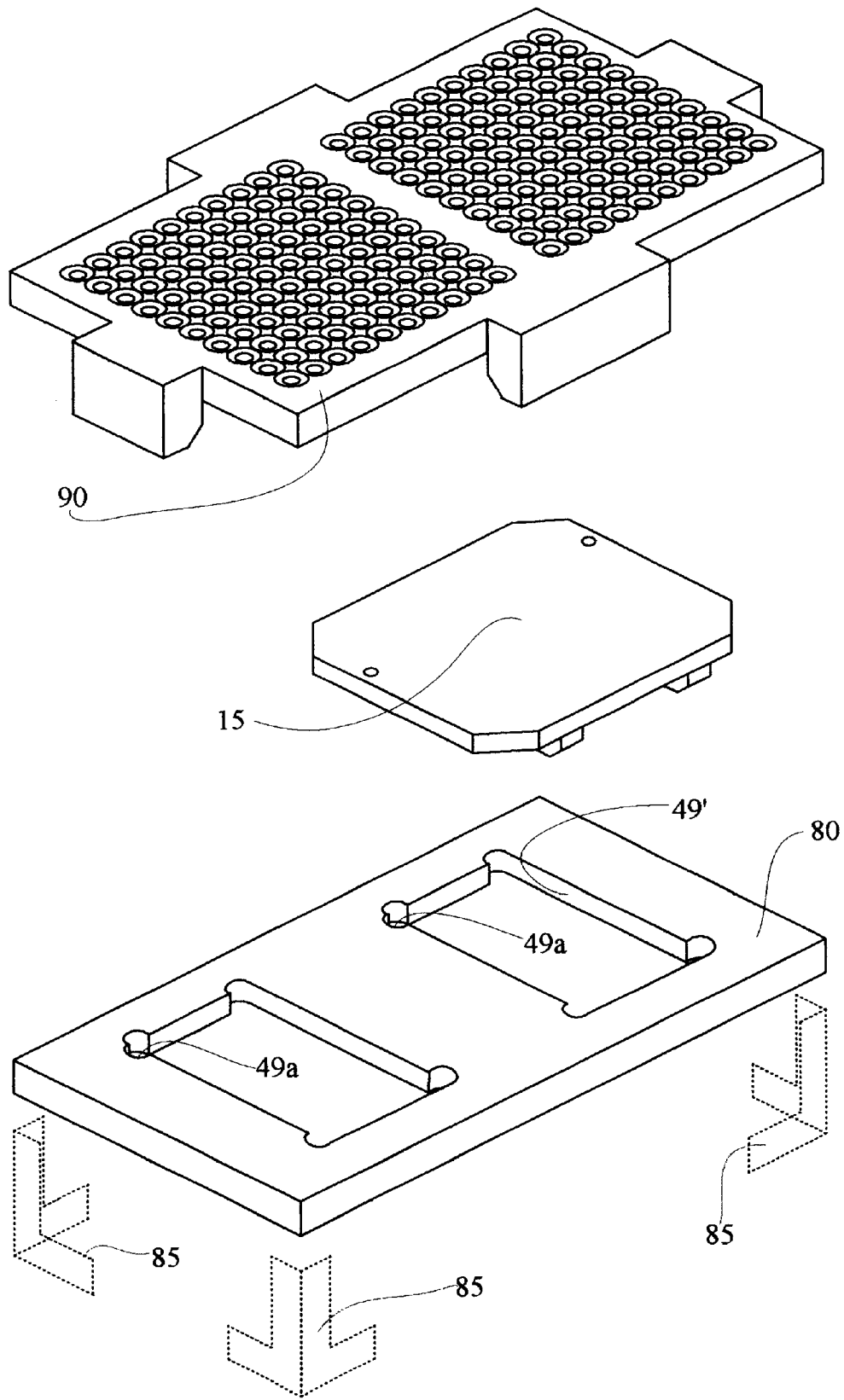
FIG. 13 is an exploded perspective view showing the alignment plate, one sample plate and the adaptor plate, where the alignment plate is provided with a 10×10 array of alignment holes in accordance with the present invention.
Figure 14:
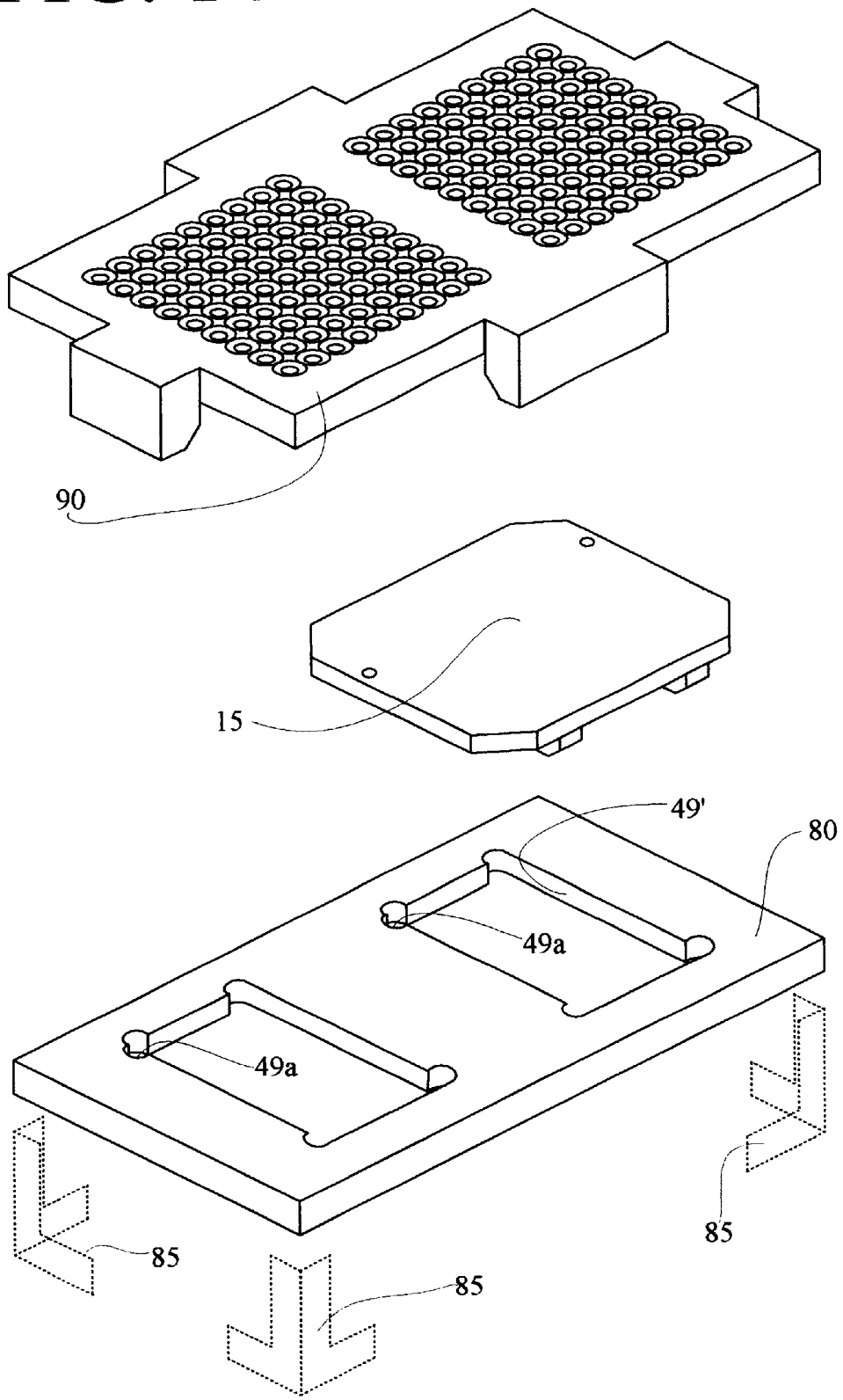
FIG. 14 is an exploded perspective view showing another alignment plate, one sample plate and the adaptor plate, where the alignment plate is provided with a 9×9 array of alignment holes in accordance with the present invention.

FIG. 13 is an exploded perspective view showing the first alignment plate 90, one sample plate 15 and the adaptor plate 80, where the first alignment plate is provided with a 10×10 array of alignment holes. In a manner similar to the first embodiment depicted in FIGS. 4–9, a second alignment plate 98 shown in FIG. 14 is provided with a 9×9 array of alignment holes in order to load a second array of samples onto the sample plate 15.

It should be understood from the above description that the first and second alignment plates 90 and 98 allow multiple arrays of samples to be deposited on a single sample plate 15. Further the adaptor plate 80, in combination with the first and second alignment plates 90 and 98 allows for two sample plates 15 to be loaded with multiple arrays of samples.

It should also be understood that the specific number of alignment holes in the alignment plates of the present invention is not limited to the specific number shown in the drawings. The alignment plates of the present invention may be provided with an array of holes of over to 20×20 holes if desired and the size of the sample plate allows. The number of holes in any array of holes is dependent primarily upon the size of the sample plate and the size of the samples to be deposited on the sample plate.

Further, it should be understood that the present invention is not limited to the specific sample plate depicted. There are several MALDI apparatus currently available. The present invention is applicable to all. For instance, the sample plate depicted is about 2.25 inches by 2.25 inches in size. Other MALDI apparatus' use sample plates that are larger and can hold more samples. The present invention is applicable to larger sample plates as well. Specifically, the alignment plates described above can be dimensioned to fit any sample plate.

In the field of proteomics, samples to be deposited on the sample plate 15 can be prepared in a variety of ways. For example, for cellular matter analysis, the samples can be based upon processed spots initially excised from a 2-D electrophoresis gel slab. 2-D electrophoresis gel slabs are prepared in a variety of ways, for instance see U.S. Pat. No. 5,993,627, which is incorporated herein by reference in its entirety. After excising a spot from a 2-D gel, the spot is deposited in a 96-well microtiter plate (aka 96-well plate 50 depicted in FIG. 3) or microcentrifuge tube. The spot may include a specific peptide or protein that is to be subjected to mass spectrometry analysis.

Figure 15:
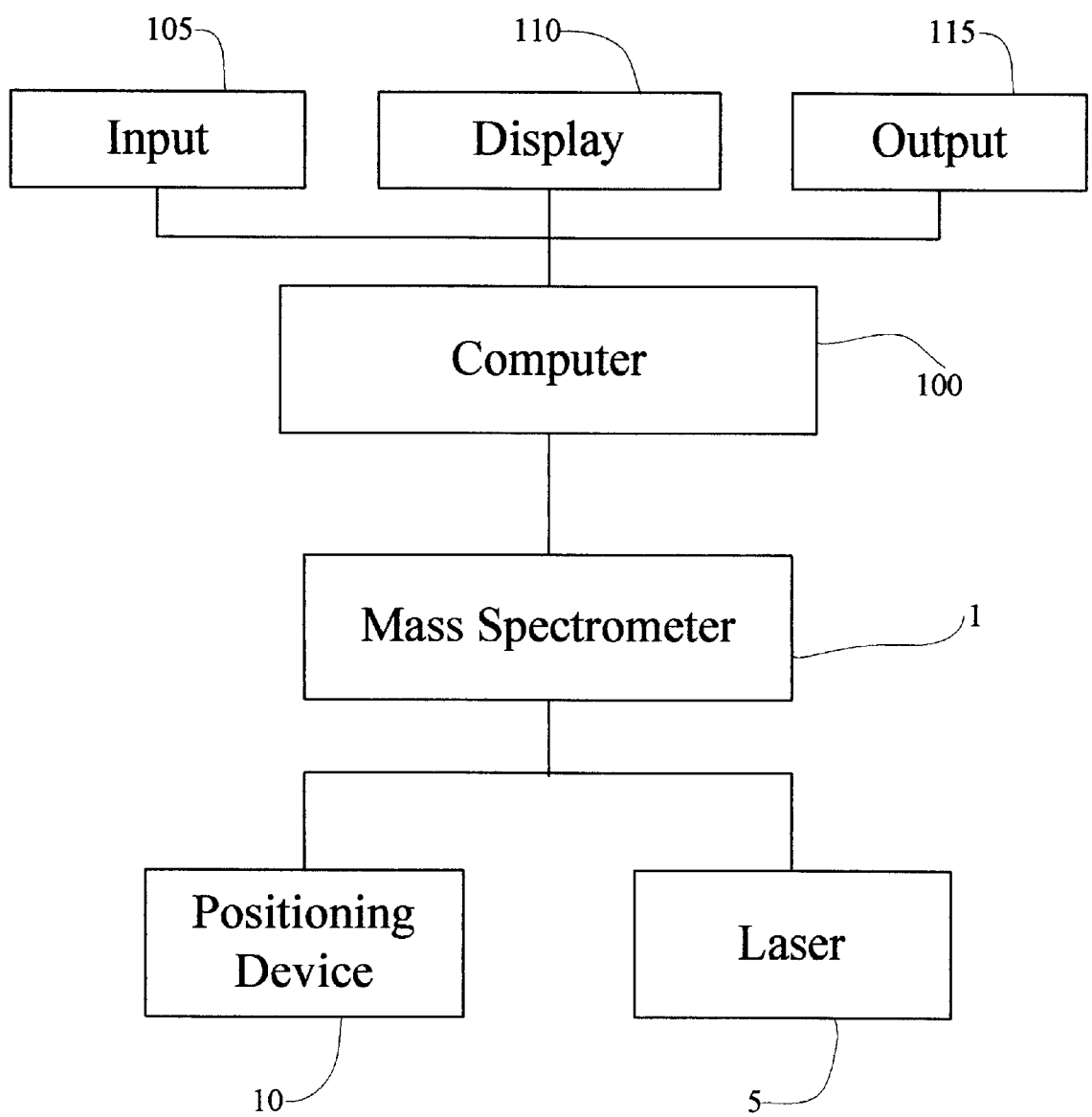
FIG. 15 is a block diagram showing the X-Y robotic apparatus and a computer for controlling the X-Y robotic apparatus in accordance with the present invention.

After loading one or more excised spots into the 96-well plate 50 or microcentrifuge tube, the 96-well plate 50 or microcentrifuge tube is then moved to an X-Y robotic apparatus, such as the X-Y robotic apparatus 48 described above with respect to FIG. 3. The X-Y robotic apparatus 48 is typically controlled by a computer 100, as shown in FIG. 15. The computer 100 typically includes an input 105 such as a keyboard, floppy disk drive and or mouse. The computer 100 also includes a display 110 and an output 115.

The X-Y robotic apparatus 48, under the control of the computer 100, performs several procedures on each of the spots in the 96-well plate 50 in order to prepare the excised spots for spotting on the sample plate. For instance, the spot, which includes gel slab material, must be digested in order to remove the unwanted gel material. Such procedures are well known in the art and vary depending upon various circumstances. However, almost all digestion procedures include manipulation of fluid in and about the 96-well plate 50 retaining the samples. There are many X-Y robotic apparatus 48 available commercially for manipulation of such liquids in the preparation of samples.

After each sample is digested, and processed for sample preparation, each sample is typically moved to a clean 96-well plate by the X-Y robotic device 48. The computer 100 records identification of the sample and its location on the sample plate 15 in memory (not shown) and is configured to output location information upon request. In the above described manner, spots excised from a 2-D gel are processed and thereafter deposited on a sample plate 15 for analysis in the MALDI apparatus 1.

An advantage of the present invention is that the X-Y robotic apparatus 48 that performs the liquid manipulation in the sample preparation procedures may now be used to spot the samples on the sample plate 15 using the alignment plates and adaptor plate described above.

By virtue of the above described alignment plates it is possible to increase the sample carrying capabilities of a sample plate of a mass spectrometry apparatus. It is further possible to more reliably position the samples on the sample plate for more reliable targeting of the laser of the mass spectrometry apparatus.

By virtue of the above described alignment plates in combination with the adaptor plate, it is possible to increase the sample carrying capabilities of a sample plate of a mass spectrometry apparatus using an X-Y robotic device that is not specifically designed for mass spectrometry sample plate loading for depositing samples on a sample plate. Specifically, using the alignment plates and adaptor plate of the present invention, it is possible to augment a liquid handling X-Y robotic device such that the X-Y robotic device may be used for unintended use, thereby broadening the usefulness of the X-Y robotic device.

While the invention has been described in detail above, the invention is not intended to be limited to the specific embodiments as described. It is evident that those skilled in the art may now make numerous uses and modifications of and departures from the specific embodiments described herein without departing from the inventive concepts.

What is claimed is:

1. A method for depositing samples on a sample plate, comprising the steps of:
   providing a sample plate on an X-Y loading device;
   installing a first alignment plate above the sample plate, the first alignment plate being formed with a plurality of alignment holes extending from one side of the first alignment plate to another side of the first alignment plate;

getting a sample using a pipette tip installed on a moveable portion of the X-Y loading device;

moving the pipette tip toward the sample plate through one of the alignment holes in the first alignment plate to guide the pipette tip to a desired location on the sample plate; and depositing the sample on the desired location on the sample plate.

2. A method as set forth in claim 1, further comprising the steps of:

removing the alignment plate from the X-Y loading device;

installing a second alignment plate on to the X-Y loading device, the second alignment plate having a plurality of alignment holes that are offset from the alignment holes in the first alignment plate; and getting another sample using the pipette tip;

moving the pipette tip toward the sample plate using one of the alignment holes in the second alignment plate to guide the pipette tip to another desired location on the sample plate; and depositing the sample on the another desired location on the sample plate.

3. A method as set forth in claim 1, wherein the sample plate is a removable part of a MALDI mass spectrometer.

4. A method as set forth in claim 1, wherein prior to said getting step, the sample is prepared by performing the following steps:

excising a spot from a 2-D electrophoresis gel; and digesting the spot to isolate bio-matter contained in the spot to produce the sample.

5. A method for depositing samples on a sample plate, comprising the steps of:

installing an adaptor plate on an X-Y loading device;

providing a sample plate on the adaptor plate;

installing a first alignment plate above the sample plate, the first alignment plate being formed with a plurality of alignment holes extending from one side of the alignment plate to another side of the first alignment plate;

getting a sample using a pipette tip installed on a moveable portion of the X-Y loading device;

moving the pipette tip toward the sample plate through one of the alignment holes of the first alignment plate to guide the pipette tip to a desired location on the sample plate; and depositing the sample on the desired location on the sample plate.

6. A method as set forth in claim 5, further comprising the steps of:

removing the first alignment plate from the adaptor;

installing a second alignment plate on to the adaptor plate, the second alignment plate having a plurality of alignment holes that are offset from the alignment holes in the first alignment plate; and getting another sample using the pipette tip;

moving the pipette tip toward the sample plate through one of the alignment holes in the second alignment plate to guide the pipette tip to another desired location on the sample plate; and depositing the sample on the another desired location on the sample plate.

7. A method as set forth in claim 5, wherein the sample plate is a removable part of a MALDI mass spectrometer.

8. A method as set forth in claim 5, wherein prior to said getting step, the sample is prepared by performing the following steps:

excising a spot from a 2-D electrophoresis gel; and digesting the spot to isolate bio-matter contained in the spot to produce the sample.

9. An aligning apparatus for guiding a pipette tip toward a sample plate for depositing samples onto the sample plate, the apparatus comprising:

an adaptor configured to receive and retain the sample plate; and an alignment plate formed with an array of alignment holes extending from one side of said alignment plate to another side of said alignment plate, each of said alignment holes being formed with a conical contour at said one side of said alignment plate for guiding a pipette tip therethrough, said alignment plate configured to engage said adaptor with said alignment holes being exposed to a surface of the sample plate.

10. An aligning apparatus as set forth in claim 9, wherein said alignment plate further comprises a plurality of positioning legs extending away from said one side, said positioning legs being engageable with said adaptor.

11. An alignment apparatus as set forth in claim 9, further comprising:

a second alignment plate formed with a second array of alignment holes, said second alignment plate being formed with a plurality of positioning legs engageable with said adaptor such that said second array of alignment holes is offset from said first array of alignment holes.

12. An alignment apparatus as set forth in claim 11, wherein said array of alignment holes comprises a 10×10 array of holes.

13. An alignment plate as set forth in claim 12, wherein said second array of alignment holes comprises a 9×9 array of holes.

14. An alignment plate as set forth in claim 9, wherein the sample plate is a removable part of a MALDI mass spectrometer.

15. A robotic apparatus for manipulating liquid samples comprising;

a table;

a robotic manipulator mounted to said table and adapted to move said table, said robotic manipulator including an end for retaining a pipette tip;

a support on said table for receiving and supporting a sample plate of a mass spectrometry apparatus; and an alignment plate removably coupled to said support for guiding said pipette tip to predetermined locations on the sample plate.

16. A robotic apparatus as set forth in claim 15, wherein said support comprises an adaptor plate configured to receive and support at least one sample plate.

17. A robotic apparatus as set forth in claim 16, wherein said alignment plate is formed with an array of alignment holes extending from one side of said alignment plate to another side of said alignment plate, each of said alignment holes being formed with a conical contour at said one side of said alignment plate for guiding the pipette tip therethrough, said alignment plate configured to engage said adaptor with said alignment holes being exposed to a surface of the sample plate.

18. A robotic apparatus as set forth in claim 17, wherein said alignment plate further comprises a plurality of positioning legs extending away from said one side, said positioning legs being engageable with said adaptor.

19. A robotic apparatus as set forth in claim 17, further comprising:
 a second alignment plate formed with a second array of alignment holes, said second alignment plate being formed with a plurality of positioning legs engageable with said adaptor such that said second array of alignment holes is offset from said first array of alignment holes.

20. A robotic apparatus as set forth in claim 19, wherein said array of alignment holes comprises a 10×10 array of holes.

21. A robotic apparatus as set forth in claim 20, wherein said second array of alignment holes comprises a 9×9 array of holes.

22. An robotic apparatus as set forth in claim 15, wherein the sample plate is a removable part of a MALDI mass spectrometer.

* * * * *